United States Patent [19]

Sansalone et al.

[11] Patent Number: 5,165,270
[45] Date of Patent: Nov. 24, 1992

[54] NON-DESTRUCTIVE MATERIALS TESTING APPARATUS AND TECHNIQUE FOR USE IN THE FIELD

[76] Inventors: Mary J. Sansalone, 27 Whitetail Dr.; Donald G. Pratt, 118 Linn St., both of Ithaca, N.Y. 14850

[21] Appl. No.: 636,336

[22] Filed: Dec. 31, 1990

[51] Int. Cl.⁵ ..................... G01N 3/30; G01N 29/10
[52] U.S. Cl. ........................................ 73/12; 73/594
[58] Field of Search ............... 73/572, 579, 584, 594, 73/12, 78, 79, 81, 82, 83, 84, 85

[56] References Cited

U.S. PATENT DOCUMENTS

| | | | |
|---|---|---|---|
| 4,177,798 | 12/1979 | Leveque et al. | 73/584 |
| 4,519,245 | 5/1985 | Evans | 73/579 |
| 4,682,490 | 7/1987 | Adelman et al. | 73/12 |
| 4,711,754 | 12/1987 | Bednar | 73/12 |
| 4,918,988 | 4/1990 | Ebihara et al. | 73/594 |
| 5,024,090 | 6/1991 | Pettigrew et al. | 73/572 |

Primary Examiner—Hezron E. Williams
Assistant Examiner—Rose M. Finley
Attorney, Agent, or Firm—Salzman & Levy

[57] ABSTRACT

The present invention features an apparatus and method for impact-echo testing of structures in situ, in the field. The impact-echo testing method provides a non-invasive, non-destructive way of determining the defects in the structure. The method is both uniform and reliable, the test procedure being substantially identical every time. The apparatus of the invention comprises a portable, hand-held unit having a plurality of impactors disposed therein. The plurality of impactors comprise a number of differently weighted spheres that are each designed to impart a different impact energy into the structure to be tested. Each sphere is disposed on a distal end of a spring-steel rod. A particular weighted sphere is chosen by a selector disposed on the testing unit. The sphere is withdrawn from the rest position by a pair of jaws to a given height above the structure. At a predetermined release point, the sphere is released, causing it to impact the structure with a specific duration and impart a given energy thereto. The impact produces stress waves that are reflected from the internal flaws and external surfaces of the structure. The reflected waves are detected by a transducer that converts the stress waves into an electrical signal (displacement waveform). The waveform is then processed to provide an amplitude spectrum, and in the case of plates, a reflection spectrum. For plates, the reflection spectrum can be interpreted by a neural network provides results that are indicative of either the thickness of the structure or of the defects disposed therein.

26 Claims, 4 Drawing Sheets

NON-DESTRUCTIVE MATERIALS TESTING APPARATUS AND TECHNIQUE FOR USE IN THE FIELD

This invention was made with Government support under PYI Award MSM-8957131 awarded by the National Science Foundation and SHRP-88-C204 SUB 2 awarded by the Strategic Highway Research Program. The Government has certain rights in the invention.

FIELD OF THE INVENTION

The invention relates to a non-destructive materials testing technique and apparatus that can be used in the field, and more particularly to a portable impact-echo apparatus and field-test method for detecting voids, cracks, and delaminations in materials, and more particularly heterogeneous materials, such as concrete.

BACKGROUND OF THE INVENTION

The present invention relates to an impact-echo analyzing apparatus and method for use in the field.

Many different methods are currently available for the non-destructive testing of materials, amongst which are: acoustic impact, infrared thermography, and ground penetrating radar. Although each of these methods is a viable technique for detecting faults and defects in materials, each has drawbacks that prevents its universal application. This is most particularly true with respect to availability in the field. No existing method provides reliability under various site conditions, nor provides the capability for rapid on-site testing of large areas. Even worse, all of the present techniques for non-destructive testing are complex and cumbersome, and are not easily applied.

The most serious problem affecting the service life of reinforced concrete structures is the formation of delaminations due to disruptive stresses. These disruptive stresses are caused by the weathering and corrosive deterioration of internal steel reinforcements.

Recently, the method of impact-echo testing of concrete slabs has been shown to provide reliable results in the detection of voids, defects and delaminations. This technique was also demonstrated to be capable of detecting delaminations in concrete slabs having asphalt overlays.

It is one thing, however, to provide a laboratory technique for analyzing concrete specimens, and another to provide the capability of performing such a test in the field. In the laboratory, the impact-echo technique produces a time-domain displacement waveform, which is then converted to an amplitude versus frequency spectrum. The frequencies obtained are indicative of the thickness of the plate and/or the depth of the internal crack or defect. It often requires an expert to interpret displacement waveforms, but amplitude spectra can be interpreted by a trained engineer. The two difficulties in converting the laboratory technique to a practical field technique are the need for: (1) a rugged, and easy to use instrument, and (2) a means for automating the signal analysis, particularly in applications requiring immediate, on site results.

The invention has developed a method of impact-echo testing of slab-like structural elements in the field. The method can be used in the field in the testing of: walls, pavements, and bridge decks. The inventive method exploits the discovery that by replacing the amplitude/frequency spectrum with a non-dimensional reflection spectrum, a more instantaneous understanding and analysis of defects in plate-like structures is achieved. The non-dimensional reflection spectrum is obtained by converting the frequency data from a fast Fourier transform of the displacement waveform, to non-dimensional depth data expressed as a percentage of the thickness according to the following equation:

$$D = C_p/2f \qquad (1)$$

where:
f is the frequency of the P wave;
$C_p$ is the P wave speed; and
D is the thickness of the test specimen or the depth of a defect;
Normalizing the depth "D" by dividing by the full thickness "T" of the structure gives the scale for the reflection spectrum.

In accordance with the invention, a neural network system has been developed for storing, analyzing, and classifying reflection spectra from other impact-echo tests on plate-like structures, such as walls, slabs, and bridge decks. The comparison of the test data with both stored flaw-free and flaw-containing data provides an instantaneous analysis of the test data at the test site. The neural network analysis developed for slab-like structures provides the test operator with information that: (1) the probability of the existence of a defect, and (2) the probable depth of the detected defect. The analysis and the data storage and retrieval can be accomplished using a portable computer so that on-site inspection and evaluation becomes a reality.

In addition, a new hand-held impact testing device has been developed that operatively connects to a portable computer programmed to process the test data. Data can be processed automatically using the neural network system, or it can be analyzed by an operator. The hand-held impact tester comprises a novel triggering apparatus, wherein different spherical impactors can be selected and released to impact a targeted test specimen. The impactors provide the proper duration of impact, whereby stress waves propagate through the test structure and reflect back from the external slab surfaces and/or internal defects in the slab. With the proper impact, voids and delaminations can be ascertained with a high probability, and the depth of the defect can be determined with precision.

The new impact tester also provides a novel sequence of testing events wherein a highly sensitive transducer is brought into contact with the work surface and electrically activated slightly prior to the contact of the spherical impactor with the test surface. Thereafter, the impact mechanism is designed to introduce stress (sound) waves into the test structure. The transducer receives the reflected waves and converts the waves into an electrical signal for processing purposes. The transducer is thereafter electrically deactivated and retracted from the test surface by the impact mechanism for return to its disarmed position.

The new impact testing device is a small, self-contained, hand-held unit. The built-in testing sequence of the self-contained testing unit provides the rapid speed that until now has never been achieved in the field.

SUMMARY OF THE INVENTION

In accordance with the present invention, there is provided an apparatus and method for impact-echo testing of structures in situ, in the field. The impact-echo testing method provides a non-invasive, non-destructive means for determining the defects in the structure. The method is both uniform and reliable, the test procedure being substantially identical every time.

The apparatus of the invention comprises a portable, hand-held unit having a plurality of impactors disposed therein for testing structures for defects. The plurality of impactors comprise a number of differently weighted spheres that are each designed to produce a different duration of impact, thereby imparting different stress waves into the structure to be tested. The different stress waves have different frequency values depending on the impact duration. Each sphere is disposed on a distal end of a spring-steel rod. A particular weighted sphere is chosen by a selector disposed on the testing unit. At the start of the test, the selected sphere is in the resting position. The sphere is withdrawn from the rest position by a pair of jaws to a given height above the structure. This action deflects the spring-steel rod, thus increasing the potential energy of the impact sphere. At a predetermined release point, the sphere is released causing it to impact the structure and impart a given energy to the slab. The impact produces stress (sound) waves that are reflected from the external surfaces and/or internal defects of the structure. The reflected waves are detected by a transducer that converts the normal surface displacements caused by the waves into an electrical signal. The electrical signal is then processed to provide an amplitude/frequency spectrum indicative of either the thickness of the structure or the defects disposed therein.

A hand-held trigger mechanism arms and positions the transducer into contact with the structure just prior to the release of the impactor, so that the data acquisition circuitry is not triggered when the transducer is brought into contact with the structure's surface. Afterward, the transducer generates an electrical signal that is proportional to the induced surface displacement. Thereafter, the transducer is returned to a retracted position with the release of the trigger mechanism.

A portable computer electrically connected to the transducer processes the signal (time domain waveform) and provides an amplitude/frequency spectrum, which is displayed upon the computer screen. The computer program designed for analyzing plate-like structures provides neural network processing of the amplitude/frequency spectrum which gives the probability that a defect exists at any particular level in the structure.

BRIEF DESCRIPTION OF THE DRAWINGS

A complete understanding of the present invention may be obtained by reference to the accompanying drawings, when considered in conjunction with the detailed description in which:

FIG. 1b depicts a typical displacement waveform produced in a test structure utilizing the impact-echo test apparatus shown in FIG. 1a;

FIG. 3 illustrates a schematic side view of the hand-held impact testing apparatus shown in FIG. 1a;

DESCRIPTION OF THE PREFERRED EMBODIMENT

Generally speaking, the invention features a method and apparatus for conducting impact-echo testing of structures in situ, in the field. The structures of most interest to this invention are plate-like concrete structures with or without internal steel reinforcement. An impact of a selected energy level is imparted to a concrete structure to produce stress waves in the structure. These waves reflect from the external surfaces and internal defects in the concrete structure back to the impact site. A transducer responsive to the surface displacements caused by the reflected waves produces an electrical signal (waveform), which is then processed to provide an amplitude/frequency spectrum.

For the sake of clarity and brevity, like components and elements will have the same designations throughout the figures.

Figure 1A:
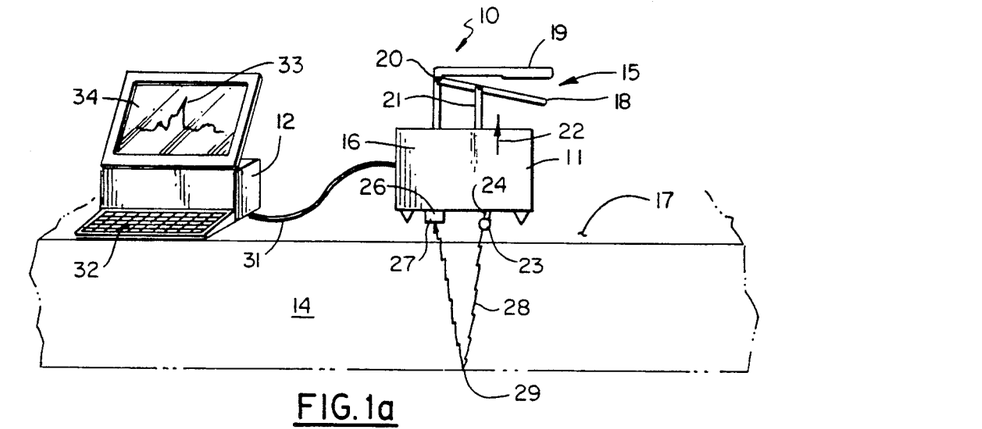
FIG. 1a illustrates a schematic of the impact-echo test apparatus of this invention.

Now referring to FIG. 1a, a schematic diagram of the testing apparatus 10 of this invention is shown in situ. The apparatus 10 comprises a hand-held testing unit 11 and a portable, computer 12. The apparatus 10 is easily transported to the field site where tests are to be conducted upon, for example, a slab of concrete 14.

The testing unit 11 comprises a hand-held trigger 15 that actuates the internal mechanism (not shown) contained in housing 16.

Figure 3:
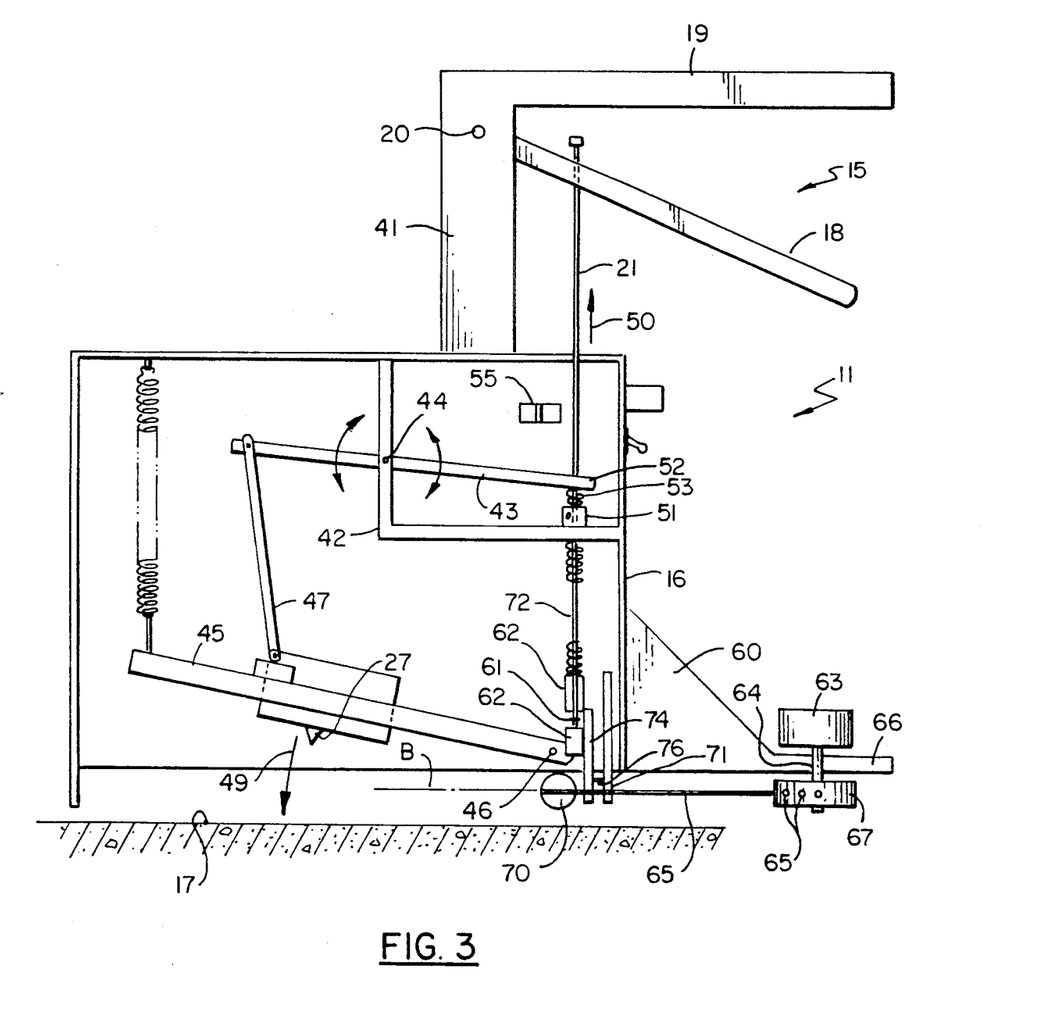

When a test is to be performed upon the concrete structure 14, an impactor selection is dialed on the hand-held unit 11, shown in FIG. 3. Next, the unit 11 is placed on the top surface 17 of the slab 14, as illustrated. The trigger 15 is then squeezed by the hand of the test operator. The lower arm 18 of the trigger 15 is pivotably attached to the upper arm 19 at pivot point 20. When the trigger 15 is squeezed, the lower arm 18 pulls the link rod 21 upward as shown by arrow 22. The link rod 21 extends into the housing 16 of unit 11, where it actuates an internal mechanism as it moves upward. When actuated, the internal mechanism accomplishes a number of sequential events. A jaw 25 (shown in FIG. 5) pulls upward upon a spring-steel rod 24 attached to a weighted impacting ball 23. Simultaneously therewith, a transducer 26 having a piezoelectric tip 27 is brought into contact with surface 17 of the slab 14. When the trigger 15 is fully squeezed, the jaw 25 releases the spring-steel rod 24, causing the weighted impacting ball 23 to impact with surface 17, as illustrated. The impact with surface 17 causes stress waves 28 to propagate in slab 14. When the propagating waves 28 reach the external surface 29 of the slab 14, the wave 28 is reflected back towards the transducer 26, as shown.

The transducer 26 is responsive to the surface displacements produced by the reflected waves 28 and generates an electrical signal. The transducer 26 is electrically connected to the portable, computer 12 via line 31. The electrical signal is fed to computer 12 where, for the case of plate-like structures, it is analyzed and compared with stored data of typical impact-echo tests.

When the computer 12 detects that a test has been performed, the surface displacement waveform and an amplitude/frequency spectrum 33 are displayed upon the display screen 34. For plate-like structures a reflection spectrum is displayed along with the neural network analysis, including probability data and information. The reflection spectrum and probability data and information provide an accurate and precise indication of the thickness of slab 14 or the location of internal defects, such as, voids and cracks.

Figure 2:
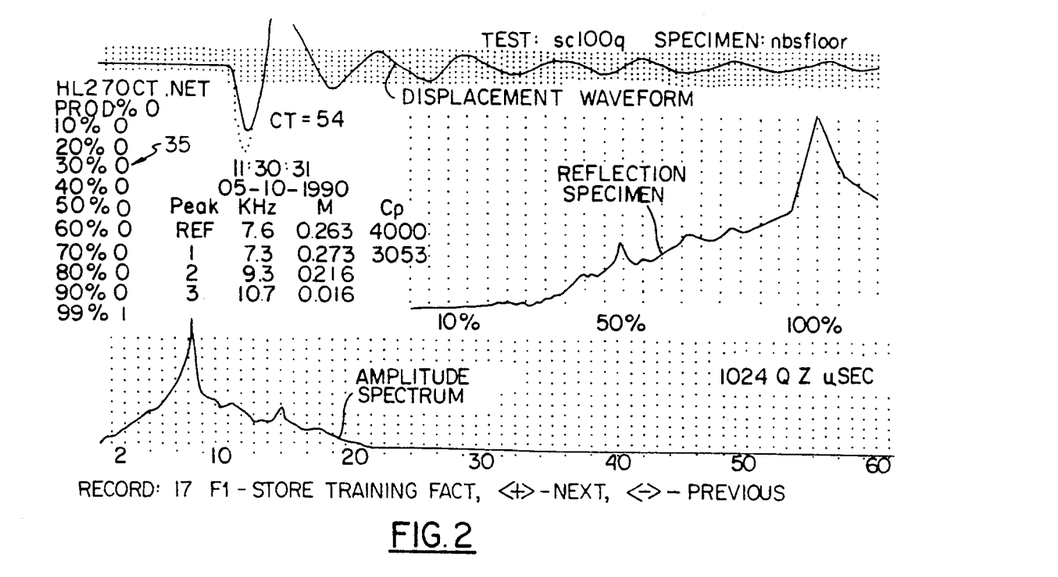
FIG. 2 shows a typical reflection spectrum and flaw probability table displayed upon the computer screen of FIG. 1a, and produced from the processed displacement waveform shown on the top of the screen, in accordance with the impact-echo test of the invention.

As aforementioned, augmenting the amplitude/frequency spectrum (shown in FIG. 2) with a non-dimensional reflection spectrum also shown in FIG. 2, aids in detecting the defect in the plate-like structure. The non-dimensional reflection spectrum is obtained by converting the frequency data obtained from fast fourier transform of the displacement waveform to non-dimensional depth data expressed as a percentage of the thickness according to the following equation:

$$D = C_p/2f \quad (1)$$

where:

f is the frequency of the P wave;
$C_p$ is the P wave speed; and
D is the thickness of the test specimen or the depth of a defect;
Normalizing the depth "D" by dividing by the full thickness "T" of the structure gives the scale for the reflection spectrum.

Figure 1B:
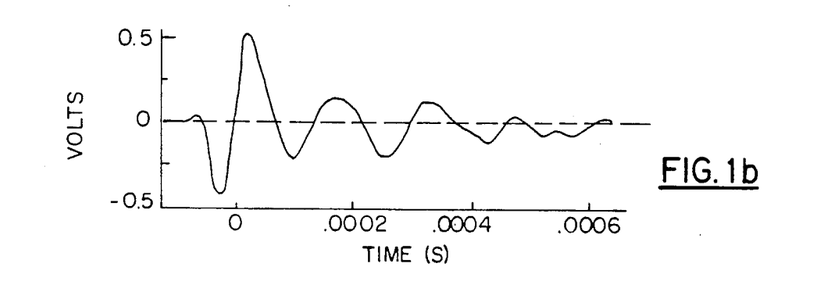
Figure 4:
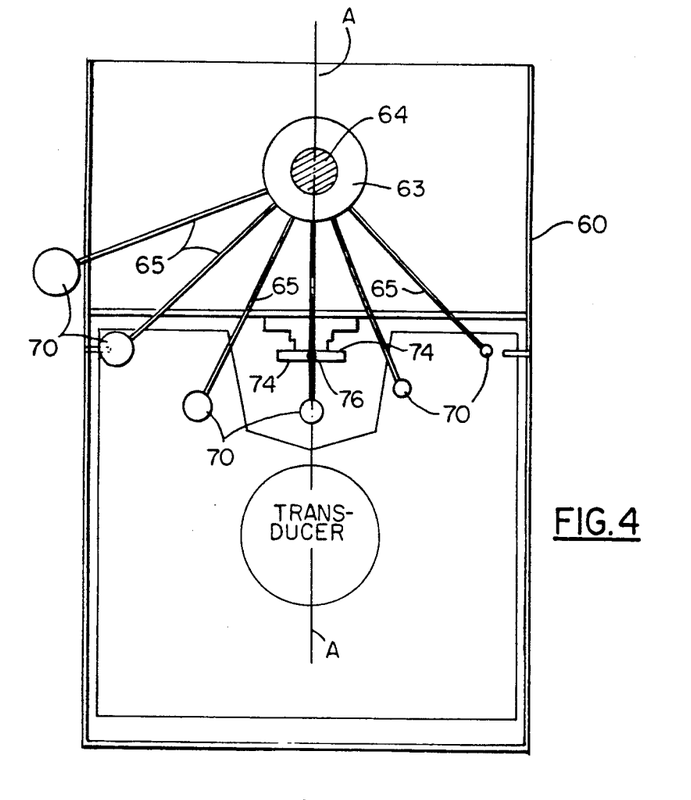
FIG. 4 depicts a top view of the testing apparatus of FIG. 3, showing the impact selector mechanism in greater detail.
Figure 5:
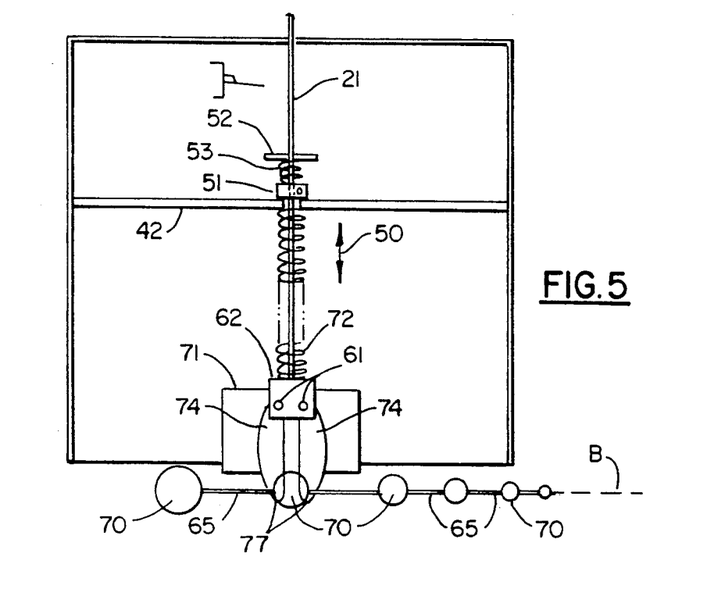
FIG. 5 shows a vertical sectional view of the impactor capture/release mechanism for the testing apparatus illustrated in FIG. 4.

Referring to schematic FIGS. 3, 4 and 5, the unit 11 illustrated in FIG. 1, is depicted in greater detail. The unit 11 comprises a housing 16 and a hand grip trigger section 15 consisting of a handle 19, trigger 18, and a rigid vertical post 41. The trigger 18 is pivotably secured to handle 19 about pivot pin 20 disposed in the vertical post 41.

A rigid frame 42 is disposed within the housing 16. The frame 42 supports a pivoting arm 43 about a pivot pin 44. The pivoting arm 43 is pivotably actuated by control rod 21 that is movably secured to trigger 18. When the trigger 18 is squeezed against handle 19, the rod 21 is caused to move upwardly, as shown by arrow 50. A locking collar 51 attached to link 21 behind the right end 52 of the pivoting arm 43 is caused to compress the coil spring 53, thus initiating the counterclockwise pivoting of the arm 43 about pivot pin 44.

A platform 45 is pivotably secured to housing 16 via pivot pin 46. The pivoting platform 45 is connected to pivoting arm 43 via a cross-bar linkage 47, and is caused to pivot when pivoting arm 43 is caused to pivot. A transducer 26 is carried upon the pivoting platform 45. The transducer 26 has a piezoelectric tip 27 that is caused to contact the concrete slab surface 17 (arrow 49) when the pivoting arm 43 and the pivoting platform 45 are both caused to pivot in a counterclockwise direction.

Shortly after the contact of the transducer tip 27 upon the slab surface 17, the right end 52 of pivot arm 43 is caused to contact limit switch 55 in its upward movement. When the limit switch 55 is closed, the transducer 26 becomes electrically operative. The transducer 26 is now able to convert displacements caused by waves 28 travelling to the surface 17 into an electrical signal for processing by the computer 12 (FIG. 1a) via line 31.

It should be obvious that the stress waves 28 must be detectable at the proper moment in time. Unit 11 provides proper sequencing of apparatus elements with the same squeezing of trigger 18, by ensuring that the impact of a selected weighted impactor with the concrete surface is accomplished slightly after transducer contact and activation.

Unit 11 has a flange 60 disposed upon the right side of housing 16, as shown. Flange 60 carries a plurality of impactors in the form of weighted balls 70, each of which is carried upon a spring-steel rod 65 attached to a rotatable hub 67. Hub 67 is rotatably secured in selected index positions about flange 60 by means of shaft 64 that is movably secured in the end section 66 of flange 60. The shaft 64 is also affixed to a rotatable selector knob 63.

Prior to the triggering of unit 11, a particular weighted ball 70 is selected for impact with surface 17 by means of the selector knob 63. There can be up to six weighted balls 70 in the preferred embodiment, each capable of imparting a different duration impact to the concrete. Selector knob 63 is detented along axis "A" to provide discrete indexing when choosing a particular impact ball 70. The knob 63 is rotated either clockwise or counterclockwise to position an impact ball 70 along the "A" axis. It is in this position that the selected impact ball 70 is withdrawn to a given height above the horizontal axis "B", and then released for downward travel and impact with surface 17. In being withdrawn to a given height above the horizontal axis "B", the spring-steel rod 65 that secures the ball 70 to hub 67, is caused to bend. The bent rod 65 stores a given spring potential, wherein the ball 70 impacts with surface 17 with a given, predetermined energy.

Different duration impacts are required for the impact-echo testing of concrete slabs 14, because different frequencies are needed for thicker slabs and flaws located at different depths. The theory of the impact-echo testing of this invention will be explained in greater detail hereinafter.

A selected ball 70 is withdrawn to a given height above horizontal axis "B" by means of a pair of flexible jaws 74 that engage with a rod 65 of a selected ball 70. The flexible jaws 74 wrap about and encompass the rod 65 in an initial untriggered state, as best shown in FIG. 5. Each jaw 74 is rotatively articulated upon platform 62 by means of hinge pin 61. The jaws 74 are spring biased to a closed, gripping position about rod 65. The platform 62 is affixed to rod 21. A coil spring 72 disposed between platform 62 and rigid frame 42, acts to bias the jaws 74 downwardly into engagement with rod 65.

When the trigger 15 is actuated, the rod 21 moves upwardly (arrow 50), causing platform 62 to rise and the jaws 74 to withdraw the selected weighted ball 70 above horizontal axis "B", via the gripped rod 65. As the ball 70 and rod 65 are caused to rise, the jaws 70 move past a stationary abutment pin 76 attached to a vertical wall member 71. As the jaws 74 move past the stationary abutment pin 76, the rod 65 is caused to engage pin 76 and slip through the gripping ends 77 of jaws 74, as best shown in FIG. 5. The abutment pin 76 is a given height above horizontal axis "B", and acts to release the rod 65 and attached ball 70. In this manner, the selected ball 70 always falls from a given height, and the rod 65 always stores a given spring energy. But because of the different diameter and mass of the impactor balls 70, each selected ball produces a different impact duration.

It will be observed that the release of a selected ball 70 coincides to, and is simultaneously operative with, the actuation of transducer 26 after contacting the concrete slab surface 17, as aforementioned. The trigger mechanism 15 via rod 21 provides the proper sequence of events, and brings all the necessary elements into play at the exact time.

It should also be obvious that the unit 11 provides a rapid, uniform procedure, wherein exacting amounts of energy are imparted to the concrete, whereby the test results are both accurate and precise.

Operation of the Impact-Echo Test

In impact-echo testing, a stress pulse is introduced into the concrete by mechanical impact. The hardened steel spheres 70, ranging from 5 mm to 18 mm in diameter, strike the concrete slab 14 with an impact duration of approximately 20 to 80 microseconds. Such an impact generates a pulse comprising lower frequency waves (generally less than about 50 kHz). The pulse 28 propagates through the concrete and is reflected by cracks, voids, delaminations and external boundaries.

The transducer 26 was developed by the National Institute of Standards & Technology, and can be purchased from Industrial Quality, Inc., Gaithersburg, Md. as Model No. 501.

The distance to a defect or to the bottom of the slab 14 becomes easy to calculate using Equation (1) wherein the frequency content of the displacement waveform 28 is calculated by the fast Fourier Transform (FFT), as aforementioned.

An amplitude/frequency spectrum can be plotted from the test results of any given series of tests, but the determination of the exact location of defects in the concrete may sometimes require expert interpretation.

This invention reflects the discovery that an easier way to identify the location and probabilities of defects in a plate-like concrete structure is to represent the data as a non-dimensional reflection spectrum, assuming a constant $C_p$ and structure thickness. A peak in the spectrum occurring at 100% of the depth indicates a solid structure, whereas a peak occurring at a percentage of the depth with the absence of a peak at 100% represents a flaw at that percentage level of the depth.

The computer 12 uses neural analysis and a program named "Brainmaker" from California Scientific Software to analyze a given reflection spectrum test with stored data. The stored data can be actual test results or mathematically calculated data. A pre-processing routine acquires data and calculates the reflection spectrum, which is presented to the neural network.

A post-processing routine interprets the results of the network. The results of the neural analysis can be divided into two categories: a) classifiable results and b) anomalous results, which cannot be classified. Anomalous results can occur if the duration of the impact is too long to detect a small or a shallow flaw located at a short distance below the surface 17 of slab 14. Therefore, the inventive apparatus 10 provides the capability to choose the proper duration for the impact using selector knob 63. In the case of selection of the wrong impactor ball 70 for a small or shallow flaw, the computer screen 34 may show an output having a high flaw probability without a clear depth indication. The operator of the test would then be obliged to select a different impactor so that more definitive results can be obtained.

The neural network method comprises a pattern classification algorithm inspired by the structure of the human brain. The network is made up of layers of interconnected processing units called neurons. Each neuron is able to acquire results from other neurons, to add these results together, to perform a pre-defined mathematical operation on the sum, and to send the result to other neurons. Typically, the neurons are arranged in three layers: an input layer, a hidden layer, and an output layer. The input layer is configured so that patterns to be classified can be presented to the network by applying the points in the pattern to the neurons in the input layer. The hidden layer processes the pattern, and the output layer produces the classification and presents it to the user.

The connections between the neurons are weighted, so that the result of each connection is multiplied by a factor or "weight", prior to applying the result to the next neuron. Changing the connection weights has a dramatic effect on the results produced by the network for a given pattern. By proper adjustment of the weights, it is possible for the network to produce a specific result for a given pattern.

Connection weights are adjusted according to a training algorithm, which uses typical examples of patterns and results to "train" the network to perform the desired classification. During training, a pattern is applied and the results are computed by the network. These results are compared with the desired classification, and the difference is used to make adjustments to the connection weights in order to bring the network results closer to the desired classification. The next pattern is then applied, the results computed and compared, and more adjustments are made. The process is continued until the network can correctly classify all the patterns. The training is then completed, and the neural network is ready to classify patterns other than those used for training.

The user of the Brainmaker program can define the number of neurons in each of the layers, specify the mathematical operation to be performed by the neurons, and adjust the various parameters required to train and use a network. The current program implements the training algorithm, requiring the user to compile a set of typical patterns for training, along with the correct classification for each pattern. These patterns and results are placed in a file that is read by the program during training. Once the training file is compiled and the network parameters are initialized, training is automatically carried out by the program.

Figure 6:
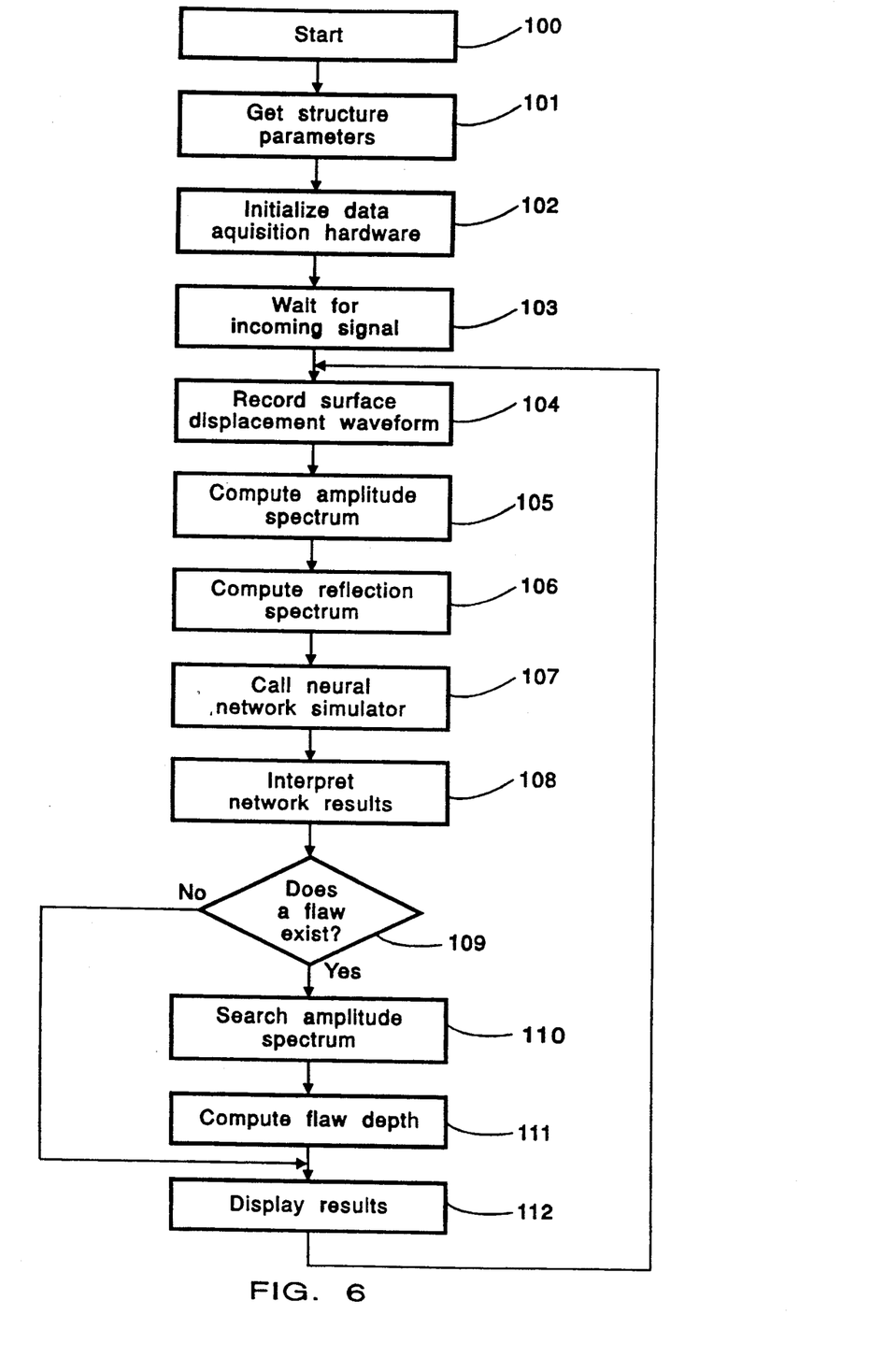
FIG. 6 depicts a flow chart of the computer program utilized by the computer shown in FIG. 1a, for the testing of plate-like structures in accordance with this invention.

Referring to FIG. 6, a flow diagram of the analysis used by computer 12 is shown. The computer 12 is initialized, step 100. Next, the structure parameters are fed into the computer 12 via keyboard 32, step 101. The test unit 11 is then initialized, step 102. The computer waits for the incoming signal from transducer 26 via line 31, step 103. The surface displacement waveform supplied by the transducer 26 is recorded, step 104.

An amplitude spectrum is calculated using the fast Fourier transform, step 105. A reflection spectrum is provided, step 106.

The processor then invokes the neural network simulation, step 107. The results of the neural network analysis are then interpreted, step 108. Essentially, the program calculates the probabilities of a flaw existing at different percentage levels of the reflection spectrum. If a flaw is determined to exist, step 109, the amplitude spectrum is searched for the peak in the region indicated to have the flaw, step 110. The amplitude spectrum is used to calculate the frequency value of a peak because greater precision can be obtained utilizing this calculation than using the reflection spectrum. The depth of the flaw is then computed based upon the maximum peak found in the amplitude spectrum for the flaw region, step 111. The results of the computer analysis are then displayed on the computer screen 34, step 112. The computer 12 then waits for the next incoming signal, step 103, and the process is repeated.

If the decision is made that there is no flaw in the concrete slab, step 109, the results are displayed on the computer screen, step 112, and the computer awaits the next signal, step 103.

Referring to a typical display output 33, as shown in FIG. 2, there is shown a no-flaw condition, as indicated by the probability table at left, referred to generally as reference numeral 35. A reflection spectrum at the right shows the maximum peak at 100% indicating the thickness of the slab. An amplitude spectrum at bottom shows the frequency at the value corresponding to reflection from the bottom of the slab (Equation 1). The waveform displayed at the top of the screen is the received signal (transducer output).

Since other modifications and changes varied to fit particular operating requirements and environments will be apparent to those skilled in the art, the invention is not considered limited to the example chosen for purposes of disclosure, and covers all changes and modifications which do not constitute departures from the true spirit and scope of this invention.

Having thus described the invention, what is desired to be protected by Letters Patent is presented by the subsequently appended claims.

What is claimed is:

1. An impact device for generating impact-echo signals in structures, comprising:
    a triggering mechanism for initiating an impact sequence of events in the echo-impact testing of a structure;
    a transducer operatively connected to said triggering mechanism for detecting reflected impact signals traveling through said structure being tested, and generating an electrical signal in response thereto;
    an impact mechanism connected to said triggering mechanism for introducing a selectable duration impact for generating stress waves for propagation within said test structure, said generated stress waves being frequency-dependent upon the duration of the selected impact, and said frequency being related to thickness of said structure, whereby the selection of said impact duration provides a means by which a structure and its flaws can be measured; and
    activating means operatively connected to said impact mechanism, said transducer, and said trigger mechanism for activating said transducer in operative sequence with the introduction of the impact signal in said test structure.

2. The impact device for generating impact-echo signals in structures in accordance with claim 1, wherein said activating means includes means for mechanically moving said transducer from a first, electrically deactivated, non-contact position with respect to said test structure, to a second, active, contact position with said test structure, in response to said trigger mechanism initiation.

3. The impact device for generating impact-echo signals in structures in accordance with claim 2, wherein said activating means includes an arming system that is armed to activate said transducer, after said transducer is mechanically moved to said second contact position.

4. The impact device for generating impact-echo signals in structures in accordance with claim 1, wherein said impact mechanism includes a number of differently weighted impactors, and means to selectively choose, arm and release these impactors.

5. The impact device for generating impact-echo signals in structures in accordance with claim 1, further comprising a portable computer operatively connected to said transducer for receiving the electrical signal therefrom for processing same into defect information.

6. The impact device for generating impact-echo signals in structures in accordance with claim 4, wherein said weighted impactors include a plurality of spheres each disposed on a distal end of a spring member.

7. The impact device for generating impact-echo signals in structures in accordance with claim 6, wherein said trigger mechanism includes a biased jaw-like member for engaging with, and thereafter releasing, one of said spring members in order to impart a spring induced kinetic force to one of said plurality of spheres.

8. The impact device for generating impact-echo signals in structures in accordance with claim 2, wherein said activating means includes means for returning said transducer to its first, non-contact, electrically deactivated position.

9. The impact device for generating impact-echo signals in structures in accordance with claim 8, wherein said means for returning said transducer to its first, non-contact, electrically deactivated position further includes means for deactivating said transducer.

10. An impact device for generating impact-echo signals in structures, comprising:
    a triggering mechanism for initiating an impact sequence of events in the echo-impact testing of a structure;
    a transducer operatively connected to said triggering mechanism for detecting reflected impact signals traveling through said structure being tested, and generating an electrical signal in response thereto;
    an impact mechanism connected to said triggering mechanism for introducing a selected duration impact for generating stress waves for propagation within said test structure; and
    activating means operatively connected to said impact mechanism, said transducer, and said trigger mechanism for activating said transducer in operative sequence with the introduction of the impact signal to said test structure, including means for mechanically moving said transducer from a first electrically deactivated, non-contact position with respect to said test structure, to a second, active, contact position with said test structure, in response to said trigger mechanism initiation.

11. The impact device for generating impact-echo signals in structures in accordance with claim 10, wherein said activating means includes an arming system that is armed to activate said transducer, after said transducer is mechanically moved to said second contact position.

12. The impact device for generating impact-echo signals in structures in accordance with claim 10, wherein said impact mechanism includes a number of differently weighted impactors, and means to selectively choose, arm and release these impactors.

13. The impact device for generating impact-echo signals in structures in accordance with claim 10, further comprising a portable computer operatively connected to said transducer for receiving the electrical signal therefrom for processing same into defect information.

14. The impact device for generating impact-echo signals in structures in accordance with claim 12, wherein said weighted impactors include a plurality of spheres each disposed on a distal end of a spring member.

15. The impact device for generating impact-echo signals in structures in accordance with claim 14, wherein said trigger mechanism includes a biased jaw-like member for engaging with, and thereafter releasing, one of said spring members in order to impart a spring induced kinetic force to one of said plurality of spheres.

16. The impact device for generating impact-echo signals in structures in accordance with claim 10, wherein said activating means includes means for returning said transducer to its first, non-contact electrically deactivated position.

17. The impact device for generating impact-echo signals in structures in accordance with claim 16, wherein said means for returning said transducer to its first, non-contact, electrically deactivated position further includes means for deactivating said transducer.

18. An impact device for generating impact-echo signals in structures, comprising:
- a triggering mechanism for initiating an impact sequence of events in the echo-impact testing of a structure;
- a transducer operatively connected to said triggering mechanism for detecting reflected impact stress waves traveling through said structure being tested, and generating an electrical signal in response thereto;
- an impact mechanism connected to said triggering mechanism for introducing a selected duration impact for generating stress waves for propagation within said test structure; and
- activating means operatively connected to said impact mechanism, said transducer, and said trigger mechanism for activating said transducer substantially simultaneously with the introduction of the impact stress waves to said test structure.

19. The impact device for generating impact-echo signals in structures in accordance with claim 18, wherein said activating means includes means for mechanically moving said transducer from a first, electrically deactivated, non-contact position with respect to said test structure, to a second, active, contact position with said test structure, in response to said trigger mechanism initiation.

20. The impact device for generating impact-echo signals in structures in accordance with claim 19, wherein said activating means includes an arming system that is armed to activate said transducer, after said transducer is mechanically moved to said second contact position.

21. The impact device for generating impact-echo signals in structures in accordance with claim 18, wherein said impact mechanism includes a number of differently weighted impactors, and means to selectively choose, arm and release these impactors.

22. The impact device for generating impact-echo signals in structures in accordance with claim 18, further comprising a portable computer operatively connected to said transducer for receiving the electrical signal therefrom for processing same into defect information.

23. The impact device for generating impact-echo signals in structures in accordance with claim 21, wherein said weighted impactors include a plurality of spheres each disposed on a distal end of a spring member.

24. The impact device for generating impact-echo signals in structures in accordance with claim 6, wherein said trigger mechanism includes a biased jaw-like member for engaging with, and thereafter releasing, one of said spring members in order to impart a spring induced kinetic force to one of said plurality of spheres.

25. The impact device for generating impact-echo signals in structures in accordance with claim 19, wherein said activating means includes means for returning said transducer to its first, non-contact, electrically deactivated position.

26. The impact device for generating impact-echo signals in structures in accordance with claim 25, wherein said means for returning said transducer to its first, non-contact, electrically deactivated position further includes means for deactivating said transducer.

* * * * *